United States Patent [19]

Stahly et al.

[11] Patent Number: 4,476,315

[45] Date of Patent: Oct. 9, 1984

[54] NUCLEOPHILIC SUBSTITUTION PROCESS

[75] Inventors: G. Patrick Stahly; Barbara C. Stahly, both of Baton Rouge, La.

[73] Assignee: Ethyl Corporation, Richmond, Va.

[21] Appl. No.: 452,616

[22] Filed: Dec. 23, 1982

Related U.S. Application Data

[63] Continuation-in-part of Ser. No. 373,633, Apr. 30, 1982.

[51] Int. Cl.$^3$ .............................................. C07C 79/46
[52] U.S. Cl. ....................................... 560/20; 562/434; 562/438; 560/46; 560/55; 560/21; 560/23; 548/473; 548/470; 548/472
[58] Field of Search ...................... 560/20, 46, 55, 21, 560/23; 548/470, 472, 473

[56] References Cited

PUBLICATIONS

Golenski J., Tetrahedron Letter, No. 37, pp. 3495–3498.
Mokosza M., J. Org. Chem. 1980, 45, 1534–1535.
Mokosza M., Int. Conf. Biotechnol. Biol., Act. Nat. Prod. (Proc), 1st, 1981, Issue 2, pp. 480–490.

*Primary Examiner*—Paul J. Killos
*Attorney, Agent, or Firm*—Donald L. Johnson; John F. Sieberth; Patricia J. Hogan

[57] ABSTRACT

Nitroarylacetic acid esters are prepared by reacting a nitroaromatic compound which is devoid of halogen on the aromatic ring carrying a nitro group with an alpha,alpha-disubstituted acetic acid ester in an inert solvent and in the presence of a base so that the ester undergoes a nucleophilic substitution on an unsubstituted ring carbon of the nitroaromatic compound during which an alpha-substituent functions as a leaving group. Nitrobenzene acetic acids and their esters are useful intermediates for the synthesis of pharmaceuticals.

29 Claims, No Drawings

NUCLEOPHILIC SUBSTITUTION PROCESS

CROSS-REFERENCE

This application is a continuation-in-part of copending application Ser. No. 373,633, filed Apr. 30, 1982, now abandoned.

TECHNICAL FIELD

This invention relates to nitroarylacetic acid esters and derivatives thereof—more particularly to processes for preparing the esters and derivatives.

BACKGROUND

It is known that nitrobenzene acetic acids and their esters are particularly useful intermediates for the synthesis of pharmaceuticals. For example, 2-[4-(1,3-dihydro-1-oxo-2H-isoindol-2-yl)phenyl]propionic acid—an anti-inflammatory and analgesic agent commonly known as indoprofen—can be prepared from a 2-(4-nitrobenzene)propionic acid intermediate by hydrogenating the intermediate, reacting the resultant 2-(4-aminobenzene)propionic acid with phthalic anhydride, and reducing the resultant 2-(4-phthalimidophenyl)propionic acid, e.g., with zinc and formic acid. Also, 2-[4-(1,3-dihydro-1-oxo-2H-isoindol-2-yl)phenyl]butyric acid—commonly known as indobufen—can be formed in a similar manner from 2-(4-nitrobenzene)butyric acid.

In the past, a disadvantage of employing nitrobenzene acetic acid or esters as pharmaceutical intermediates has been the difficulty of preparing those intermediates by conventional techniques. For example, 2-(4-nitrobenzene)propionic acid has been customarily formed by a three-step procedure wherein (1) 4-ethylnitrobenzene is reacted with sodium phenoxide and carbon dioxide to produce disodium 2-methyl-2-(4-nitrobenzene)malonate, (2) the malonate salt is converted by acidification into the corresponding diacid, and (3) the diacid is heated to effect decarboxylation.

It would obviously be a welcome contribution to the art to provide a method of synthesizing nitrobenzeneacetic acid esters and analogs and derivatives thereof in a simple, straightforward manner.

STATEMENT OF INVENTION

An object of this invention is to provide novel processes for preparing nitroarylacetic acid esters.

Another object is to provide such processes which permit the preparation of the esters is good yield with high selectivity in a very simple and straightforward manner.

A further object is to provide novel, improved processes for preparing derivatives of nitroarylacetic acid esters.

These and other objects are attained by (A) reacting a nitroaromatic compound which is devoid of halogen on the aromatic ring carrying a nitro group with an alpha,alpha-disubstituted acetic acid ester in an inert solvent and in the presence of a base so that the ester undergoes a nucleophilic substitution on an unsubstituted ring carbon of the nitroaromatic compound during which an alpha-substituent functions as a leaving group, thereby forming a nitroarylacetic acid ester, and (B) when appropriate, converting the nitroarylacetic acid ester to a desired derivative thereof.

DETAILED DESCRIPTION

Nitroaromatic compounds utilizable in the practice of the invention include a variety of such compounds—the chief requirements for their utility being that (1) they bear at least one nitro substituent on an aromatic ring, (2) they contain at least one replaceable hydrogen on an aromatic ring to which a nitro group is attached, and (3) they be devoid of substituents which would interfere with the desired nucleophilic substitution reaction.

Thus, the utilizable nitroaromatic compounds include compounds having one or more simple or fused aromatic rings containing five to six members and either bearing no substituents other than nitro substituents or also bearing any of a variety of inert substituents, i.e., substituents that do not interfere with the desired nucleophilic substitution reaction, such as alkyl, alkoxy, alkylmercapto, trifluoromethyl, dialkylamino, dialkanoylamino, cyano, dialkylcarbamoyl, alkylsulfonyl, dialkylsulfamoyl, alkoxyalkyl, haloalkyl, cycloalkyl, halocycloalkyl, etc.—any alkyl chains in the substituents generally being lower alkyl, i.e., $C_1$-$C_6$ alkyl, chains. When the nitroaromatic compound contains more than one ring, any such inert substituent may be on the same ring as the ring bearing a nitro substituent and/or on a ring which is directly or indirectly attached to the ring bearing a nitro substituent, and any such inert substituent may be a halo substituent if it is on a ring other than a ring carrying a nitro group.

When the aromatic ring bearing the required nitro substituent is a six-membered ring, there will be at least one replaceable hydrogen in a position para or ortho to the carbon bearing the nitro substituent; and it is preferred that there be a replaceable hydrogen in the para position. Nitroaromatic compounds having a five-membered ring should have a replaceable hydrogen on a carbon adjacent to, or separated by two ring atoms from, the carbon bearing the nitro substituent.

Illustrative of nitroaromatic compounds that may be used in the practice of the invention are heterocyclic compounds which preferably contain five or six-membered rings having aromatic character, such as nitropyridine-N-oxide, 5-nitroisoquinoline, 5- and 6-nitroquinolines, 2-nitrothiophene, etc.; fused-ring aromatic compounds, such as the 1- and 2-nitronaphthalenes, etc.; aromatic compounds containing a plurality of simple rings, such as the 2-, 3-, and 4-nitrobiphenyls, the 2-, 3-, and 4-benzylnitrobenzenes, 2-nitrodiphenyl ether, etc.; and aromatic compounds containing a single simple ring, such as nitrobenzene, 2-methylnitrobenzene, the 2,3-, 2,5-, and 3,5-dimethylnitrobenzenes, the 2,4- and 2,6-diethylnitrobenzenes, 3,4-dibutylnitrobenzene, the 1,2- and 1,3-dinitrobenzenes, 2,6-dinitrotoluene, the 1,2,3- and 1,2,4-trinitrobenzenes, 2-nitro-N,N-diethylaniline, 4-nitro-N-ethylacetanilide, 2-nitrobenzylcyanide, 2-nitrophenyl acetate, etc.

In some cases, polynitroaromatic reactants may undergo substitution reactions whereby one of the nitro groups is replaced by the ester reactant. Therefore, the possibility of this competitive reaction should be kept in mind when selecting a polynitroaromatic for use in the process.

The preferred nitroaromatic compounds are nitrobenzenes having a replaceable hydrogen in the position para to the nitro group, since the nucleophilic substitution reaction of the invention tends to be highly selective on the para position, and the use of such compounds therefore leads to the production of nitrobenzeneacetic acid esters which are ideally suited for the synthesis of anti-inflammatory agents of the type mentioned above. Particularly preferred is nitrobenzene, which is readily converted with high selectivity into pharmaceutically-active agents such as 2-[4-(1,3-dihydro-1-oxo-2H-isoindol-2-yl)phenyl]propionic acid, 2-[4-(1,3-dihydro-1-oxo-2H-isoindol-2-yl)phenyl]butyric acid, and analogs thereof.

The alpha,alpha-disubstituted acetic acid esters that can be used in the practice of the invention also include a variety of such compounds, which—in general—may be represented by the formula:

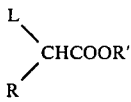

wherein L is a leaving group; R is halo (preferably chloro) or more preferably a hydrocarbyl (e.g., alkyl, alkenyl, alkynyl, cycloalkyl, cycloalkenyl, aryl, aralkyl, etc.) or hydrocarbyloxyhydrocarbyl (e.g., alkoxyalkyl, aryloxyalkyl, alkoxyaryl, alkoxycycloalkyl, etc.) group which most preferably contains up to about 10 carbons; and R' is a hydrocarbyl group which preferably contains up to about 10 carbons and most preferably is an alkyl group.

Exemplary leaving groups, L, include halo, aryloxy, haloaryloxy, alkylthio, cycloalkylthio, arylthio, aralkylthio, haloalkylthio, halocycloalkylthio, haloarylthio, haloaralkylthio, or—less preferably—alkoxy, cycloalkoxy, aralkoxy, haloalkoxy, halocycloalkoxy, haloaralkoxy, and the like, as well as other suitable leaving groups which have been described in the literature, e.g., in Golinski et al., "'Vicarious' Nucleophilic Substitution of Hydrogen in Aromatic Nitro Compounds," *Tetrahedron Letters*, Vol. 37, pp. 3495-8 (1978) and in Makosza et al., "Vicarious Substitution of Hydrogen in Aromatic Nitro Compounds with Acetonitrile Derivatives," *Journal of Organic Chemistry*, Vol. 45, pp. 1534-5 (1980).

When the leaving group is an organic group, it is generally preferred that the group contain not more than about 10 carbons, although organic leaving groups having an even higher carbon content are satisfactory in the practice of the invention. Preferably, the leaving group is halo, i.e., chloro, bromo, fluoro, or iodo; and it is more preferably chloro or bromo, most preferably chloro.

Exemplary of utilizable alpha,alpha-disubstituted acetic acid esters are alpha-chloropropionates such as methyl, ethyl, propyl, isopropyl, butyl, t-butyl, cyclohexyl, phenyl, and benzyl 2-chloropropionates; the corresponding alpha-bromopropionates; and other alpha-substituted monocarboxylic acid esters such as methyl 2-methylmercaptopropionate; ethyl 2-butylmercaptopropionate, methyl 2-phenoxybutyrate, phenyl 2-methylmercaptopropionate, butyl 2-cyclohexylmercaptovalerate, methyl 2-(4-fluorophenoxy)propionate, and the like. The alpha-halo-alpha-hydrocarbylacetic acid esters, i.e., esters of alpha-halomonocarboxylic acids containing at least three carbons, are especially preferred, although similar esters in which the alpha-halo substituent is replaced by one of the other leaving groups mentioned above are also highly desirable.

In another highly desirable embodiment of the invention, the alpha,alpha-disubstituted acetic acid ester is an alpha,alpha-dihaloacetic acid ester, most preferably an alpha,alpha-dichloroacetic acid ester, which leads to the formation of a product having a reactive halo substituent in the alpha-position, e.g., a product corresponding to the formula:

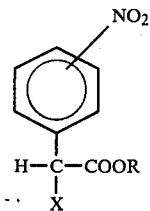

wherein X is halo, preferably chloro, and R is a hydrocarbyl group, preferably containing up to about 10 carbons. Such products enable facile synthesis of a variety of end products. Most preferably the nitro group is in the position para to the ester substituent, although it may be located in an ortho position.

The solvent used in a nucleophilic substitution process of the invention may be any solvent that is inert under the conditions of the reaction, i.e., any solvent that will not prevent the reaction from occurring. Such solvents are substantially anhydrous and are generally aprotic, although solvents such as liquid ammonia are also utilizable.

Illustrative aprotic solvents which may be employed in the process of the invention include ethers such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines such as pyridine, N-ethylpiperidine, triethyl amine, tributyl amine, N,N-diphenyl-N-methyl amine, N,N-dimethylaniline, etc.; and other aprotic solvents. However, the preferred aprotic solvents are dipolar aprotic solvents such as dimethyl sulfoxide, N,N-dimethylformamide, N,N-dimethylacetamide, dimethyl sulfone, tetramethylene sulfone, N-methylpyrrolidinone, and the like.

Bases useful in the practice of the invention include all bases strong enough to activate the ester reactant, e.g., alkaline earth metal compounds such as calcium oxide, calcium hydride, calcium hydroxide, barium oxide, barium hydroxide, magnesium hydroxide, zinc hydroxide, etc. However, the base is preferably an alkali metal compound, e.g., an organoalkali metal compound, alkali metal hydride, alkali metal hydroxide, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethylsulfoxide), sodium hydride, potassium hydride, sodium hydroxide, potassium hydroxide, sodium oxide, potassium oxide, sodium amide, potassium amide, lithium diisopropylamide, sodium methoxide, potassium t-butoxide, the sodium salt of the monomethylether of ethylene glycol, sodium phenoxide, and the like. Ordinarily the use of sodium hydride, potassium hydride, or potassium t-butoxide will be found most convenient and economical.

Use of an alkali metal compound as the base permits the alternatives of using the alkali metal compound alone or in conjunction with a phase transfer catalyst, such as a quaternary ammonium salt, ethylene glycol, or a suitable crown ether. When a phase transfer catalyst is employed (1) the alkali metal compound may be any of the alkali metal compounds generically or specifically indicated above, although the type of alkali metal compound being used determines the type of crown ether that is preferably utilized—lithium bases generally calling for the use of a 12-crown-4 ether, sodium bases generally calling for the use of a 15-crown-5 ether, and potassium bases generally calling for the use of an 18-crown-6 ether, and (2) the reaction medium may be any of the aprotic solvents mentioned above, or it may be an inert liquid hydrocarbon such as benzene, toluene, xylene, hexane, heptane, isooctane, or the like.

When an alkali metal hydride, especially a highly pure alkali metal hydride, is employed as the base, it is desirable to include a small amount of a transfer agent such as water, alcohol, or the like in the system. It is believed that the transfer agent activates the hydride by reacting therewith to form a small amount of the alkali metal hydroxide or alcoholate.

The nitroarylacetic acid ester synthesis of the invention is conducted in a substantially anhydrous reaction system, and accordingly, except when a small amount of water (which is itself consumed by reaction with the alkali metal hydride) is employed as a transfer agent, the components of the reaction system should be brought together and maintained under a dry inert atmosphere. Thus, while it is possible to conduct the process in the presence of air, it is desirable to maintain the reaction system under an atmosphere of dry nitrogen or the like. Since the reaction itself is normally an exothermic reaction, with its initiation readily ascertainable by noting the exotherm produced, the reactants are ordinarily brought together at ambient temperatures, although the temperature may be raised or lowered to suit the needs of the occasion if desired.

The nitroaromatic compound and alpha,alpha-disubstituted acetic acid ester may be used in amounts such as to provide a stoichiometric excess of either of the reactants or the stoichiometric amount of each. However, when a stoichiometric excess of the nitroaromatic compound is employed, the quantity of product obtainable will be limited by the quantity of ester used, so it is desirable to utilize a stoichiometric excess of the ester. The amount of base employed is preferably such as to provide at least two molar equivalents of base per mol of nitroaromatic compound, since the use of smaller amounts—although permitting the reaction to occur—makes the base the limiting reagent.

The mode of addition of the ingredients of the reaction system is not particularly critical. Accordingly, it is convenient to add the nitroaromatic compound to a mixture of the other materials, add the base to a mixture of the other materials, add the reactants to a mixture of the base and inert solvent, introduce all four ingredients simultaneously into the reaction zone, or the like. Since the reaction ordinarily proceeds very rapidly, long reaction times are not required. The reaction will usually be completed within a matter of minutes or a few hours at ambient temperatures.

When derivatives of the nitroarylacetic acid esters are desired, they may be prepared by employing conventional techniques to convert to the desired derivatives the nitroarylacetic acid esters made in accordance with the present invention. Thus, for example:

(A) an alkyl 2-(4-nitrobenzene)propionate synthesized by the process of this invention may be hydrogenated to an alkyl 2-(4-aminobenzene)propionate, which in turn may be reacted with phthalic anhydride to form an alkyl 2-(4-phthalimidophenyl)propionate, which may be reduced and hydrolyzed to 2-[4-1,3-dihydro-1-oxo-2H-isoindol-2-yl)phenyl]propionic acid, and (B) an alkyl 2-(4-nitro-3-phenoxybenzene)propionate synthesized by the process of this invention may be hydrogenated to an alkyl 2-(4-amino-3-phenoxybenzene)propionate, which in turn may be deaminated to form an alkyl 2-(3-phenoxybenzene)propionate, which may then be hydrolyzed to 2-(3-phenoxybenzene)propionate, a pharmaceutical commonly known as fenoprofen, etc.

The particular conventional techniques used to convert the nitroarylacetic acid esters into their various derivatives are not critical. It may sometimes be desirable to use certain particular techniques for the preparation of the derivatives, e.g., the techniques taught in Section No. 8(c), pages 2–11, of Adria Laboratories' NDA on Indoprofen Capsules, on file with the Federal Drug Administration, the disclosures of which are incorporated herein by reference. However, the overall processes for preparing the derivatives are simplified and made more efficient and economical by the present simplification of the synthesis of the nitroarylacetic acid esters, regardless of the particular techniques used to convert them into their various derivatives.

As indicated above, the present invention is particularly advantageous in providing a readier and more economical route to the synthesis of pharmaceuticals and other chemical products that can be prepared from nitroarylacetic acid esters. Such products include, not only those mentioned above, but a variety of products, such as products disclosed in U.S. Pat. Nos. 3,641,040, 3,657,230, 3,767,805, 3,868,391, 3,936,467, 3,993,763, 3,997,669, 4,010,274, 4,118,504, 4,126,691, 4,163,788, and 4,239,901.

The following examples are given to illustrate the invention and are not intended as a limitation thereof.

EXAMPLE 1

Into a flame-dried flask fitted with a mechanical stirrer, under nitrogen, were placed 3.6 g (0.09 mol) of 60% NaH in mineral oil. This was washed with three 15 ml portions of petroleum ether (b.p. 35°–60° C.), dried in a nitrogen stream, and slurried in 25 ml of N,N-dimethylformamide which had been stored over 3-Angstrom molecular sieves. Then ten drops of a solution of 5.0 g (0.041 mol) of nitrobenzene and 5.5 g (0.045 mol) of methyl 2-chloropropionate in 5 ml of dimethylformamide were added to the NaH slurry. After about 3 minutes the mixture became deep purple in color and an exotherm was noted, indicating the reaction had begun. The rest of the reactant solution was added dropwise to the NaH slurry over 22 minutes and an ice-water bath was periodically applied to the flask so that the temperature remained between 20° and 30° C. The mixture was allowed to stir for 15 minutes at 20°–30° C. after the addition was complete and was then poured into 200 ml of 1N HCl. This aqueous mixture was extracted with three 150 ml portions of diethyl ether. The ether layers were combined, dried over magnesium sulfate, and concentrated to give 10 g of brown oil. Gas chromatographic analysis of this oil indicated it contained 6.9% nitrobenzene and 54% methyl 2-(4-nitrobenzene)propionate. From the oil were distilled 4.6 g of 96% methyl 2-(4-nitrobenzene)propionate (0.5 mm, 125° C.).

EXAMPLE 2

A reaction was carried out as described in Example 1 but was worked up as follows: The reaction mixture was poured into 200 ml of water, and the resulting aqueous mixture (pH 12.9) was successively extracted with three 150 ml portions of petroleum ether (b.p. 35°-60° C.), three 150 ml portions of toluene, three 150 ml portions of diethyl ether, and three 150 ml portions of dichloromethane. Gas chromatographic analyses indicated that essentially all of the methyl 2-(4-nitrobenzene)propionate was located in the petroleum ether extracts. These were combined, dried (magnesium sulfate) and concentrated to give 3.7 g of an oil containing 59% methyl 2-(4-nitrobenzene)propionate. From the oil were distilled 2.0 g of 94% methyl 2-(4-nitrobenzene)propionate (0.5 mm, 125° C.).

EXAMPLE 3

Another reaction was carried out as in Example 1 except that the workup was as follows: The reaction mixture was poured into 200 ml of water, and 96% sulfuric acid was added until the pH was 6.9. The resulting aqueous mixture was successively extracted with three 150 ml portions of petroleum ether (b.p. 35°-60° C.), three 150 ml portions of toluene, three 150 ml portions of diethyl ether, and three 150 ml portions of dichloromethane. Gas chromatographic analyses indicated that essentially all of the methyl 2-(4-nitrobenzene)propionate was contained in the petroleum ether extracts. These were combined, dried (magnesium sulfate), and concentrated to give 4.4 g of an oil containing 71% methyl 2-(4-nitrobenzene)propionate.

EXAMPLE 4

A reaction mixture formed as in Example 1 was worked up as follows: The reaction mixture was poured into 200 ml of water, and 96% sulfuric acid was added until the pH was 2.9. The resulting aqueous mixture was then successively extracted with three 150 ml portions of petroleum ether (b.p. 35°-60° C.), three 150 ml portions of toluene, three 150 ml portions of diethyl ether, and three 150 ml portions of dichloromethane. Gas chromatographic analyses indicated that most of the methyl 2-(4-nitrobenzene)propionate was in the petroleum ether extracts, although some was contained in the toluene extracts. The petroleum ether layers were combined, dried with magnesium sulfate, and concentrated to give 4.8 g of an oil containing 72% methyl 2-(4-nitrobenzene)propionate. The toluene extracts were combined, dried with magnesium sulfate, and concentrated to give 3.5 g of an oil containing 5.0% methyl 2-(4-nitrobenzene)propionate.

EXAMPLE 5

The following workup procedure was applied to another reaction mixture formed as in Example 1: The reaction mixture was poured into a solution of 1.25 ml of 96% sulfuric acid in 200 ml of water. About 3 ml of a black oil settled to the bottom of the aqueous mixture and were removed. The oil was triturated with three 10 ml portions of petroleum ether (b.p. 35°-60° C.), and the petroleum ether layers were combined and dried over magnesium sulfate. The dried layers were concentrated to give 1.3 g of oil (fraction 1) containing 72% methyl 2-(4-nitrobenzene)propionate (by gas chromatographic analysis). The aqueous mixture was extracted with three 150 ml portions of petroleum ether, and the organic layers were combined, dried (magnesium sulfate) and concentrated to give 2.7 g of an oil (fraction 2) containing 77% methyl 2-(4-nitrobenzene)propionate. Then the black oil that had separated from the water was recombined with the water layer, and the resulting mixture was extracted with three 150 ml portions of diethyl ether. The ether layers were combined, dried (magnesium sulfate) and concentrated to give 5.3 g of an oil (fraction 3) containing 39% methyl 2-(4-nitrobenzene)propionate.

EXAMPLE 6

Fraction 2 from Example 5 (2.7 g of oil containing 77% methyl 2-(4-nitrophenyl)propionate) was added to 5 ml of 5N NaOH, and the resulting heterogeneous mixture was stirred vigorously under nitrogen for 1.5 hours. The mixture became homogeneous during this time. It was extracted with three 10 ml portions of dichloromethane, and the organic layers were combined, dried with magnesium sulfate, and concentrated to give 0.37 g of an oil containing 88% nitrobenzene and 2% methyl 2-(4-nitrobenzene)propionate (by gas chromatographic analysis). The aqueous layer was cooled with an ice-water bath and acidified with 37% HCl. The solid which precipitated was removed by filtration and dried under high vacuum overnight to give 1.1 g of crude 2-(4-nitrobenzene)propionic acid (m.p. 64°-68° C.).

EXAMPLE 7

Into a flame-dried 1-liter flask fitted with a mechanical stirrer, under nitrogen, were placed 18.0 g of 60% NaH in mineral oil (0.450 mol) and 100 ml of N,N-dimethylformamide (stored over 3-Angstrom molecular sieves). To the resulting slurry were added 50 drops of a solution of 25.0 g of nitrobenzene (0.203 mol) and 27.5 g of methyl 2-chloropropionate (0.224 mol) in 25 ml of N,N-dimethylformamide. After about 6 minutes the mixture became deep purple in color and an exotherm was noted, indicating the reaction had begun. The rest of the reactant solution was added dropwise to the NaH slurry over 30 minutes, and an ice-water bath was periodically applied to the flask so that the temperature remained between 20° and 30° C. The mixture was allowed to stir for 20 minutes at 20°-30° C. after the addition was complete and was then poured into 1 liter of 1N HCl. This aqueous mixture was extracted with three 500 ml portions of dichloromethane. The organic layers were combined, dried (magnesium sulfate), and concentrated to give 142 g of black liquid. From this liquid was distilled 79.1 g of N,N-dimethylformamide (fraction 1, 10 mm, 30°-70° C.), followed by 34.6 g of orange oil (fraction 2, 10 mm, 65°-180° C.) which contained 7.0% nitrobenzene (by gas chromatographic analysis), 75% methyl 2-(4-nitrobenzene)propionate (by gas chromatographic analysis) and some mineral oil (observed as an insoluble upper layer).

Into 20 ml of 5N NaOH were placed 20.0 g of fraction 2 (15 g of methyl 2-(4-nitrobenzene)propionate, 0.072 mol) and the resulting mixture was stirred vigorously under nitrogen and cooled in a 25° C. water bath. The mixture became homogeneous after 20 minutes. After 90 minutes the mixture was extracted with three 30 ml portions of dichloromethane, and the aqueous layer was stirred at 50° C. under aspirator vacuum to remove residual dichloromethane. The aqueous solution was cooled in an ice-water bath, and 37% HCl was added dropwise to a pH of 7. The cooling bath was removed, 200 mg of Calgon CPG decolorizing carbon (−70 mesh) were added, the mixture was stirred for 10 minutes, and the carbon was removed by filtration through Celite. The filtrate was cooled in an ice-water bath, and 37% HCl was added to a pH of 1. The precipitated solid was removed by filtration, washed with 25 ml of cold 1N HCl, and dried at 1 mm for 19 hours over phosphorus pentoxide to give 13.3 g of 2-(4-nitrobenzene)propionic acid (m.p. 83°-85° C.).

EXAMPLE 8

Into a flame-dried flask under nitrogen were placed 140 mg (1.3 mmols) of potassium t-butoxide and 1 ml of N,N-dimethylformamide (DMF). This solution was cooled by the use of an ice water bath, and a solution of 78.1 mg (0.63 mmol) of nitrobenzene and 99.8 mg (0.64 mmol) of 87% methyl 2-chlorobutyrate in 0.5 ml of DMF was added dropwise thereto. The resulting purple mixture was stirred at ice water temperatures for 15 minutes, after which it was poured into 20 ml of 1N HCl. The aqueous mixture was extracted with three 20 ml portions of diethyl ether; and the ether layers were combined, dried over magnesium sulfate, and concentrated to give 260 mg of dark oil. Purification of this oil by preparative thin layer chromatography afforded 13 mg (8%) of t-butyl 2-(4-nitrobenzene)butyrate and 76 mg (57%) of methyl 2-(4-nitrobenzene)butyrate.

EXAMPLE 9

Into a flame-dried flask under nitrogen were placed 5.0 g (45 mmols) of potassium t-butoxide, and 50 ml of ammonia were condensed into the flask using a dry ice condenser to give a solution of the base in refluxing ammonia. A mixture of 2.7 g (22 mmols) of nitrobenzene and 2.7 g (22 mmols) of methyl 2-chloropropionate was added dropwise to the ammonia solution, and the mixture was allowed to react for 15 minutes. Then 2.5 g of ammonium chloride were added, and the ammonia was allowed to evaporate. The residue was placed in 150 ml of 1N HCl, and the aqueous mixture was extracted with three 100 ml portions of diethyl ether. The ether layers were combined, dried over magnesium sulfate, and concentrated to give 4.7 g of an oil. Gas chromatographic analysis of the oil (with internal standard) indicated it contained 2.8 g (61%) of methyl 2-(4-nitrobenzene)propionate.

EXAMPLE 10

Nine syntheses were conducted by reacting a nitroaromatic compound with methyl 2-chloropropionate in the presence of sodium hydride that had been washed free of mineral oil with pentane. In each case, 2 equivalents of the sodium hydride and 1-2 ml of DMF were placed into a flame-dried flask under nitrogen. Then a solution of 1 equivalent each of the nitroaromatic compound and the chloroester in 1-2 ml of DMF was added dropwise, and the resulting solution was stirred for 15 minutes, after which it was poured into 20-40 ml of 1N HCl. The aqueous mixture was extracted with three 20-40 ml portions of diethyl ether and the ether layers were combined, dried over magnesium sulfate, and concentrated to give a crude product mixture which was purified by preparative thin layer chromatography. The nitroaromatic compounds employed, the products obtained, and the yields are shown in Table 1.

TABLE 1

| Run | Nitroaromatic Compound | Product(s) | Yield |
|---|---|---|---|
| A | m-dinitrobenzene | methyl 2-(2,4-dinitrobenzene)propionate | 26% |
| B | o-dinitrobenzene | methyl 2-(3,4-dinitrobenzene)propionate | 58% |
| C | methyl 2-nitrobenzoate | methyl 2-(3-methoxycarbonyl-4-nitrobenzene)propionate | 50% |
| D | 2-nitroanisole | methyl 2-(3-methoxy-4-nitrobenzene)propionate | 17% |
| E | 2-nitrobenzonitrile | methyl 2-(3-cyano-4-nitrobenzene)propionate | 63% |
| F | 2-nitrothiophene | methyl 2-(2-nitro-4-thiophene)propionate + methyl 2-(2-nitro-3-thiophene)propionate | 41%* |
| G | 2-trifluoromethylnitrobenzene | methyl 2-(4-nitro-3-trifluoromethylbenzene)propionate | 35% |
| H | 3-trifluoromethylnitrobenzene | methyl 2-(4-nitro-2-trifluoromethylbenzene)propionate | 11% |
| I | 2-nitrobiphenyl | methyl 2-(4-nitro-3-phenylbenzene)propionate | 11% |

*combined yield

EXAMPLE 11

The process described in Example 10 was used to react nitrobenzene with allyl 2-chloropropionate. The product, obtained in 39% yield, was allyl 2-(4-nitrobenzene)propionate.

EXAMPLE 12

The process described in Example 10 was used to react nitrobenzene with t-butyl 2-chloropropionate, except that the sodium hydride was replaced with potassium t-butoxide. The product, obtained in 53% yield, was t-butyl 2-(4-nitrobenzene)propionate.

EXAMPLE 13

Part A

A solution of 2.9 g (26 mmols) of potassium t-butoxide in 20 ml of N,N-dimethylformamide (DMF) was generated in a flame-dried flask under nitrogen and cooled with an ice water bath. Then a solution of 3.0 g (13 mmols) of 93% 2-phenoxynitrobenzene and 1.6 g (13 mmols) of methyl 2-chloropropionate in 2.0 ml of DMF was added dropwise to the catalyst solution, and the resulting purple mixture was stirred at 0°-5° C. for 15 minutes and poured into 200 ml of 1N HCl. The aqueous mixture was extracted with three 150 ml portions of diethyl ether. The ether layers were combined, dried over magnesium sulfate, and concentrated to give 6.0 g of red oil. Chromatography of this oil on 100 g of silica gel (230-400 mesh) with 40% dichloromethane/60% petroleum ether (b.p. 35°-60° C.) as eluent afforded a fraction containing 2.2 g (56%) of methyl 2-(4-nitro-3-phenoxybenzene)propionate.

Part B

A mixture of 1.0 g of methyl 2-(4-nitro-3-phenoxybenzene)propionate, 0.1 g of 7% palladium on carbon, and 20 ml of absolute ethanol was hydrogenated at 50 psig hydrogen pressure for one hour, filtered, and concentrated to give 0.96 g of oil. Thin layer chromatographic and NMR analyses of this oil showed that it contained only methyl 2-(4-amino-3-phenoxybenzene)propionate.

Part C

A solution of 0.20 g (0.74 mmol) of methyl 2-(4-amino-3-phenoxybenzene)propionate in 1.0 ml of dry tetrahydrofuran (THF) was added dropwise to a refluxing solution of 0.18 ml (1.3 mmols) of isoamyl nitrite in 4.0 ml of THF. The resulting mixture was heated at reflux for 1.5 hours, cooled to room temperature, and concentrated. The residue was subjected to preparative thin layer chromatography to yield 0.032 g (16%) of methyl 2-(3-phenoxybenzene)propionate.

EXAMPLE 14

Into a flame-dried flask under nitrogen was placed 0.10 g (2.5 mmols) of a 60% dispersion of sodium hydride in mineral oil. This was washed with three 1 ml portions of petroleum ether (b.p. 35°–60° C.) and slurried in 2.0 ml of DMF. A solution of 0.15 g (1.3 mmols) of methyl 2-chloropropionate and 0.24 g (1.3 mmols) of 2-nitrotrifluoromethylbenzene in 2 ml of DMF was added dropwise to the sodium hydride slurry. The resulting purple mixture was stirred at room temperature for 15 minutes and poured into 20 ml of 10% hydrochloric acid. The aqueous mixture was extracted with three 20 ml portions of diethyl ether, and the ether layers were combined, dried over magnesium sulfate, and concentrated. The residue was purified by preparative thin layer chromatography to give 0.12 g (35%) of methyl 2-(4-nitro-3-trifluoromethylbenzene)propionate.

EXAMPLE 15

Example 14 was repeated except that the 2-nitrotrifluoromethylbenzene was replaced with 3-nitrotrifluoromethylbenzene. The process resulted in the formation of 37 mg (11%) of methyl 2-(4-nitro-2-trifluoromethylbenzene)propionate.

EXAMPLE 16

Example 14 was repeated except that the 0.24 g (1.3 mmols) of 2-nitrotrifluoromethylbenzene was replaced with 0.25 g (1.3 mmols) of 2-nitrobiphenyl. The process resulted in the formation of 36 mg (11%) of methyl 2-(2-nitro-5-biphenylyl)propionate.

EXAMPLE 17

Example 14 was repeated except that the 0.24 g (1.3 mmols) of 2-nitrotrifluoromethylbenzene was replaced with 0.21 g (1.3 mmols) of 2-nitroacetophenone. Analysis of the residue obtained by gas chromatography-mass spectrometry revealed the presence of methyl 2-(3-acetyl-4-nitrobenzene)propionate.

EXAMPLE 18

The procedure of Example 14 was repeated with 0.15 g (3.8 mmols) of 60% sodium hydride, 0.15 g (1.3 mmols) of methyl 2-chloropropionate, and 0.21 g (1.3 mmols) of 2-nitrobenzoic acid. Analysis of the residue obtained on workup by gas chromatography indicated the presence of 36 mg (11%) of methyl 2-(3-carboxy-4-nitrobenzene)propionate.

EXAMPLE 19

The procedure of Example 14 was repeated with 0.28 g (2.5 mmols) of potassium t-butoxide, 0.15 g (1.3 mmols) of methyl 2-chloropropionate, and 0.17 g (1.3 mmols) of 3-nitrotoluene. The residue obtained on workup was purified by preparative thin layer chromatography to give 30 mg (11%) of methyl 2-(2-methyl-4-nitrobenzene)propionate.

This invention is susceptible to considerable variation within the spirit and scope of the appended claims.

We claim:

1. A process which comprises reacting a nitroaromatic compound which is devoid of halogen on the aromatic ring carrying a nitro group with an alpha,alpha-disubstituted acetic acid ester in an inert solvent and in the presence of a base so that the ester undergoes a nucleophilic substitution on an unsubstituted ring carbon of the nitroaromatic compound during which an alpha-substituent functions as a leaving group, thereby forming a nitroarylacetic acid ester.

2. The process of claim 1 wherein the nitroaromatic compound is a mononitrobenzene having an unsubstituted position para to the nitro group.

3. The process of claim 2 wherein the mononitrobenzene is nitrobenzene.

4. The process of claim 1 wherein the alpha,alpha-disubstituted acetic acid ester is an alpha-halomonocarboxylic acid ester containing at least three carbons in the acid moiety.

5. The process of claim 4 wherein the alpha-halomonocarboxylic acid ester is an alpha-chloro- or alpha-bromomonocarboxylic acid ester.

6. The process of claim 5 wherein the alpha-halomonocarboxylic acid ester is methyl alpha-chloropropionate.

7. The process of claim 1 wherein the solvent is an aprotic solvent.

8. The process of claim 7 wherein the solvent is a dipolar aprotic solvent.

9. The process of claim 1 wherein the base comprises an alkali metal compound.

10. The process of claim 9 wherein the base is an alkali metal hydride.

11. The process of claim 10 wherein the alkali metal hydride is sodium hydride or potassium hydride.

12. The process of claim 9 wherein the base is potassium t-butoxide.

13. The process of claim 1 wherein the solvent is N,N-dimethylformamide and the base is sodium hydride or potassium hydride.

14. The process of claim 1 wherein a mononitrobenzene having an unsubstituted position para to the nitro group is reacted with an alpha-halomonocarboxylic acid ester containing at least three carbons in the acid moiety in an inert solvent and in the presence of a base so that the ester undergoes a nucleophilic substitution on an unsubstituted ring carbon of the mononitrobenzene during which the alpha-halo substituent functions as a leaving group, thereby forming a nitrobenzene acetic acid ester.

15. The process of claim 14 wherein the mononitrobenzene is nitrobenzene.

16. The process of claim 14 wherein the alpha-halomonocarboxylic acid ester is an alpha-chloro- or alpha-bromomonocarboxylic acid ester.

17. The process of claim 14 wherein the alpha-halomonocarboxylic acid ester is an alkyl ester.

18. The process of claim 14 wherein the alpha-halomonocarboxylic acid ester is an alpha-halopropionic acid ester.

19. The process of claim 18 wherein the alpha-halopropionic acid ester is an alkyl alpha-chloropropionate.

20. The process of claim 14 wherein the solvent is a dipolar aprotic solvent and the base is sodium hydride, potassium hydride, or potassium t-butoxide.

21. The process of claim 14 wherein the nitrobenzene acetic acid ester is a 4-nitrobenzene acetic acid ester.

22. The process of claim 14 wherein the mononitrobenzene is nitrobenzene, the alpha-halomonocarboxylic acid ester is an alkyl alpha-chloro- or alpha-bromopropionate, the solvent is a dipolar aprotic solvent, and the base is sodium hydride, potassium hydride, or potassium t-butoxide.

23. The process of claim 14 wherein (A) nitrobenzene is reacted with an alkyl alpha-chloro- or alpha-bromopropionate to form an alkyl 2-(4-nitrobenzene)propionate and (B) the alkyl 2-(4-nitrobenzene)propionate is hydrogenated to an alkyl 2-(4-aminobenzene)propionate.

24. The process of claim 23 wherein (A) nitrobenzene is reacted with an alkyl alpha-chloro- or alpha-bromopropionate to form an alkyl 2-(4-nitrobenzene)propionate, (B) the alkyl 2-(4-nitrobenzene)propionate is hydrogenated to an alkyl 2-(4-aminobenzene)propionate and (C) the alkyl 2-(4-aminobenzene)propionate is reacted with phthalic anhydride to form an alkyl 2-(4-phthalimidophenyl)propionate.

25. The process of claim 24 wherein (A) nitrobenzene is reacted with an alkyl alpha-chloro- or alpha-bromopropionate to form an alkyl 2-(4-nitrobenzene)propionate, (B) the alkyl 2-(4-nitrobenzene)propionate is hydrogenated to an alkyl 2-(4-aminobenzene)propionate, (C) the alkyl 2-(4-aminobenzene)propionate is reacted with phthalic anhydride to form an alkyl 2-(4-phthalimidophenyl)propionate, and (D) the alkyl 2-(4-phthalimidophenyl)propionate is reduced and hydrolyzed to 2-[4-(1,3-dihydro-1-oxo-2H-isoindol-2-yl)phenyl]propionic acid.

26. The process of claim 14 wherein (A) nitrobenzene is reacted with an alkyl alpha-chloro- or alpha-bromopropionate to form an alkyl 2-(4-nitrobenzene)propionate and (B) the alkyl 2-(4-nitrobenzene)propionate is hydrolyzed to 2-(4-nitrobenzene)propionic acid.

27. The process of claim 26 wherein (A) nitrobenzene is reacted with an alkyl alpha-chloro- or alpha-bromopropionate to form an alkyl 2-(4-nitrobenzene)propionate, (B) the alkyl 2-(4-nitrobenzene)propionate is hydrolyzed to 2-(4-nitrobenzene)propionic acid, and (C) the 2-(4-nitrobenzene)propionic acid is reduced to 2-(4-aminobenzene)propionic acid.

28. The process of claim 27 wherein (A) nitrobenzene is reacted with an alkyl alpha-chloro- or alpha-bromopropionate to form an alkyl 2-(4-nitrobenzene)propionate, (B) the alkyl 2-(4-nitrobenzene)propionate is hydrolyzed to 2-(4-nitrobenzene)propionic acid, (C) the 2-(4-nitrobenzene)propionic acid is reduced to 2-(4-aminobenzene)propionic acid, and (D) the 2-(4-aminobenzene)propionic acid is reacted with phthalic anhydride to form 2-(4-phthalimidophenyl)propionic acid.

29. The process of claim 28 wherein (A) nitrobenzene is reacted with an alkyl alpha-chloro- or alpha-bromopropionate to form an alkyl 2-(4-nitrobenzene)propionate, (B) the alkyl 2-(4-nitrobenzene)propionate is hydrolyzed to 2-(4-nitrobenzene)propionic acid, (C) the 2-(4-nitrobenzene)propionic acid is reduced to 2-(4-aminobenzene)propionic acid, (D) the 2-(4-aminobenzene)propionic acid is reacted with phthalic anhydride to form 2-(4-phthalimidophenyl)propionic acid, and (E) the 2-(4-phthalimidophenyl)propionic acid is reduced to 2-[4-(1,3-dihydro-1-oxo-2H-isoindol-2-yl)phenyl]propionic acid.

* * * * *